United States Patent
Jaax (10) Patent No.: US 9,233,247 B2
(45) Date of Patent: Jan. 12, 2016

(54) NEUROMODULATION OF RENAL NERVE FOR TREATMENT OF HYPERTENSION

(71) Applicant: BOSTON SCIENTIFIC NEUROMODULATION CORPORATION, Valencia, CA (US)

(72) Inventor: Kristen Jaax, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/201,889

(22) Filed: Mar. 9, 2014

(65) Prior Publication Data

US 2014/0277253 A1     Sep. 18, 2014

Related U.S. Application Data

(60) Provisional application No. 61/801,425, filed on Mar. 15, 2013, provisional application No. 61/808,226, filed on Apr. 4, 2013.

(51) Int. Cl.
 *A61N 1/36* (2006.01)
 *A61N 1/365* (2006.01)

(52) U.S. Cl.
 CPC ........ *A61N 1/36117* (2013.01); *A61N 1/36139* (2013.01); *A61N 1/36514* (2013.01)

(58) Field of Classification Search
 None
 See application file for complete search history.

(56) References Cited

U.S. PATENT DOCUMENTS

| 6,895,280 | B2 | 5/2005 | Meadows et al. |
|---|---|---|---|
| 2009/0005859 | A1* | 1/2009 | Keilman ................. 623/1.42 |
| 2012/0059431 | A1* | 3/2012 | Williams et al. ................. 607/5 |
| 2012/0059446 | A1 | 3/2012 | Wallace et al. |
| 2013/0012866 | A1* | 1/2013 | Deem ............... A61B 18/1492 604/21 |

OTHER PUBLICATIONS

"What is MEMS Technology?" https://www.mems-exchange.org/MEMS/what-is.html. Accessed on Mar. 23, 2015.*

* cited by examiner

*Primary Examiner* — Brian T Gedeon
*Assistant Examiner* — Ankit Tejani
(74) *Attorney, Agent, or Firm* — Faegre Baker Daniels LLP (57) ABSTRACT

A system and method for treating a patient suffering from chronic hypertension. Electrical therapeutic energy is delivered to a nerve branch of a renal artery of the patient, thereby treating the chronic hypertension. Another system and method for treating a medical condition of a patient. Electrical stimulation energy is delivered to a stimulation site on the wall of a blood vessel, thereby evoking a compound action potential in a nerve branch associated with the blood vessel, sensing the evoked compound action potential at a sensing site on the wall of the blood vessel, identifying a circumferential location of the nerve branch as being adjacent the stimulation site or sensing site based on the sensed compound action potential(s), and delivering therapeutic energy to a therapeutic site on the wall of the blood vessel adjacent the circumferential location of the nerve branch, thereby modulating the nerve branch and treating the medical condition.

14 Claims, 5 Drawing Sheets

NEUROMODULATION OF RENAL NERVE FOR TREATMENT OF HYPERTENSION

RELATED APPLICATIONS DATA

The present application claims the benefit under 35 U.S.C. §119 to U.S. Provisional Application Ser. No. 61/801,425, filed Mar. 15, 2013 and U.S. Provisional Application Ser. No. 61/808,226, filed Apr. 4, 2013, which applications are all incorporated herein by reference in their entirety.

FIELD OF THE INVENTION

The present invention relates to tissue neuromodulation systems, and more particularly, to electrical neuromodulation systems for treating hypertension in patients.

BACKGROUND OF THE INVENTION

Hypertension is a health problem affecting millions of people, requiring considerable expenditure of medical resources as well as imposing significant burdens on those who suffer from this condition. Hypertension generally involves resistance to the free flow of blood within a patient's vasculature, often caused by reduced volume stemming from plaque, lesions, and the like. Because blood vessels do not permit easy flow, the patient's heart must pump at higher pressure. In addition, reduced cross-sectional area results in higher flow velocity. In consequence, a patient's blood pressure may enter into the range of hypertension, i.e. greater than 140 mm Hg systolic/90 mm Hg diastolic. For a chronic disease, such as hypertension, where the negative outcomes such as stroke come as a result of a lifetime of exposure to elevated blood pressure. Oftentimes, such elevated blood pressure can persist for up to a year until the patient is seen in a clinic for an annual check-up, after which the patient's elevated blood pressure can be corrected using conventional means.

It has been recognized that the kidneys play a key role in blood pressure regulation, and a number of hypertension treatment approaches have focused on the kidneys, providing a number of pharmaceutical compounds aimed at promoting blood to flow through these organs. One treatment option has been to destroy some or all of the nerves innervating the kidneys through ablation, a process in which an therapeutic electrode, carried in an instrument such as an endoscope, is introduced into a patient's vasculature and navigated to a position within the renal artery. Electrical energy, operating at radio frequencies sufficient to ablate nerve tissue, is delivered to the electrode, resulting in destruction of the renal nerves.

This process, of course, is irreversible and carries the possibility of undesirable side effects. For example, it is known that renal nerve ablation can lead to neuroma formation and neuropathic pain at the site of the ablative lesion. Because the ablation of renal nerves causes permanent physiological alterations to the patient, it is often very difficult, if not impossible, to re-adjust the patient's blood pressure when needed (e.g., when the patient experience severe loss of blood).

Thus, a need remains to dynamically ameliorate hypertension without permanently affecting the renal nervous system.

SUMMARY OF THE INVENTION

In accordance with one aspect of the present inventions, a neuromodulation system for use with a patient is provided. The neuromodulation system comprises a cylindrical support structure (e.g., a stent or a balloon) configured for being deployed in a blood vessel of the patient, and at least one electrode carried by the cylindrical support structure. In one embodiment, the cylindrical support structure is a resilient skeletal spring structure for urging the electrode(s) against an inner wall of the blood vessel. In another embodiment, the support structure comprises an electrically insulative material for preventing electrical energy from being radially conveyed inward from the cylindrical support structure.

The neuromodulation system further comprises a sensor configured for sensing a parameter correlatable to blood pressure of a patient. The sensor may be carried by the cylindrical support structure. In one embodiment, the sensor includes a micro-electro-mechanical-system (MEMS) capable of measuring the parameter. The sensor may be a piezoresistive strain gage, in which case, the neuromodulation system may further comprises an intraluminal catheter configured for being filled with a liquid in communication with the piezoresistive strain gage.

The neuromodulation system further comprises analog output circuitry configured for conveying electrical therapeutic energy to electrode(s), and a controller/processor coupled to the sensor and the analog output circuitry. The controller/processor is configured for comparing the sensed parameter to a first threshold, and prompting the analog output circuitry to convey the electrical therapeutic energy to electrode(s) based on the comparison. In one embodiment, the sensed parameter comprises blood pressure, and the first threshold comprises a first threshold blood pressure (e.g., 140 mm Hg systolic/90 mm Hg diastolic). In this case, the controller/processor is configured for prompting the analog output circuitry to convey the electrical therapeutic energy to electrode(s) when the sensed blood pressure is greater than the first threshold blood pressure. The controller/processor may optionally be configured for comparing the blood pressure sensed by the sensor to a second threshold blood pressure (e.g., a threshold value in the range of 100-140 mm Hg systolic/60-90 mm Hg), and prompting the analog output circuitry to cease conveying the electrical therapeutic energy to the electrode(s) when the sensed blood pressure is less than the second threshold blood pressure. The neuromodulation system may further comprise a biocompatible casing housing the analog output circuitry and the controller/processor.

In accordance with a second aspect of the present inventions, a method for treating a patient suffering from chronic hypertension is provided. The method comprises delivering electrical therapeutic energy in accordance with a set of neuromodulation parameters to a nerve branch of a renal artery of the patient, thereby treating the chronic hypertension. Such delivery of the electrical therapeutic energy may, e.g., evoke compound action potentials (CAPs) along the nerve branch or block or disrupt CAPs along the nerve branch. The electrical therapeutic energy may be delivered from at least one electrode disposed in the renal artery to the nerve branch. In this case, the method may further comprise introducing a cylindrical support structure carrying the electrode(s) into the renal artery, and configuring the cylindrical support structure so that the electrode(s) is placed against the wall of the renal artery adjacent the nerve branch.

In one method, patient has a blood pressure greater than 140 mm Hg systolic/90 mm Hg diastolic prior to the delivery of the therapeutic energy to the nerve branch, and has a blood pressure in the range of 100-140 mm Hg systolic/60-90 mm Hg diastolic during the application of the therapeutic energy to nerve branch.

An optional method further comprises sensing a parameter correlatable to blood pressure of a patient (e.g., by sensing evoked CAPs (eCAPs) at a carotid baroreceptor or a transverse aortic arch baroreceptor), and comparing the sensed parameter to a first threshold (e.g., 140 mm Hg systolic/90 mm Hg diastolic). The electrical therapeutic energy may be delivered to the nerve branch based on the comparison. If the sensed parameter comprises the blood pressure, the first threshold may comprise a first threshold blood pressure, in which case, the electrical therapeutic energy may be delivered to the nerve branch when the sensed blood pressure is greater than the first threshold blood pressure. The sensed blood pressure may be compared to a second threshold blood pressure (e.g., a threshold value in the range of 100-140 mm Hg systolic/60-90 mm Hg), in which case, the delivery of the electrical therapeutic energy to the nerve branch may be when the sensed blood pressure is less than the second threshold blood pressure.

In accordance with a third aspect of the present inventions, a therapy system for use with a patient is provided. The therapy system comprises a cylindrical support structure (e.g., a stent or a balloon) configured for being deployed in a blood vessel of the patient, a plurality of electrodes circumferentially disposed about the cylindrical support structure, a plurality of therapeutic electrodes (which may comprises the plurality of electrodes) circumferentially disposed about the cylindrical support structure respectively adjacent the plurality of electrodes, and an electrode (which may be ring electrode carried by the cylindrical support structure) configured for being deployed in the blood vessel of the patient at a location axially remote from the plurality of electrodes. In one embodiment, the cylindrical support structure is a resilient skeletal spring structure for urging the electrode(s) against an inner wall of the blood vessel. In another embodiment, the support structure comprises an electrically insulative material for preventing electrical energy from being radially conveyed inward from the cylindrical support structure.

The therapy system further comprises analog output circuitry, monitoring circuitry, and a controller/processor configured for performing at least one of a first process and a second process, which may be performed automatically. The first process comprises prompting the analog output circuitry to sequentially activate the plurality of electrodes to evoke at least one CAP in a nerve associated with the blood vessel, prompting the monitoring circuitry to activate the axially remote electrode in response to the activation of each of the plurality of electrodes to sense the at least one evoked eCAP, and identifying one of the plurality of electrodes based on the sensed eCAP(s). The second function comprises prompting the stimulation output circuitry to active the axially remote electrode to evoke at least one CAP in the nerve associated with the blood vessel, prompting the monitoring circuitry to sequentially activate the plurality of electrodes in response to the activation of the axially remote electrode to sense the eCAP(s), and identifying the one electrode based on the sensed eCAP(s). After either of the first process or the second process is performed, the controller/processor is configured for prompting the analog output circuitry to deliver therapeutic energy to the therapeutic electrode adjacent the identified electrode. In one embodiment, multiple CAPs are evoked to increase the signal-to-noise ratio of the sensed eCAPs.

In accordance with a fourth aspect of the present inventions, a method of treating a medical condition (e.g., hypertension) of a patient is provided. The method comprises delivering electrical stimulation energy to a stimulation site on the wall of a blood vessel (e.g., a renal artery), thereby evoking at least one CAP in a nerve branch associated with the blood vessel, and sensing the eCAP(s) at a sensing site on the wall of the blood vessel. One method may further comprise disposing a stimulating electrode in the blood vessel at the stimulation site, in which case, the electrical stimulation energy is delivered by the stimulating electrode, and disposing a sensing electrode in the blood vessel at the sensing site, in which case, the eCAP(s) is sensed by the sensing electrode. In one method, multiple CAPs are evoked to increase the signal-to-noise ratio of the sensed eCAPs.

The method further comprises identifying a circumferential location of the nerve branch as being adjacent one of the stimulation site and the sensing site based on the sensed eCAP(s), and delivering therapeutic energy to a therapeutic site on the wall of the blood vessel adjacent the circumferential location of the nerve branch, thereby modulating the nerve branch and treating the medical condition.

One method may further comprise disposing a plurality of stimulation electrodes in the blood vessel respectively at a plurality of circumferential sites in axial alignment with the stimulation site disposing a sensing electrode in the blood vessel at the sensing site, and sequentially activating the stimulation electrodes. The CAP(s) may be evoked by the activation of one of the stimulation electrodes. The method further comprises activating the sensing electrode in response to the activation of each of the stimulation electrodes to sense the eCAP(s), and identifying the circumferential site at which the one stimulation electrode is located as the stimulation site. This method may further comprise disposing a plurality of therapeutic electrodes in the blood vessel respectively adjacent the stimulation electrodes, and selecting the therapeutic electrode adjacent the one stimulation electrode to convey the therapeutic energy to the therapeutic site. A cylindrical support structure carrying the stimulation electrodes and therapeutic electrodes may be disposed in the blood vessel in axial alignment with the stimulation site.

Another method may further comprise disposing a plurality of sensing electrodes in the blood vessel respectively at a plurality of circumferential sites in axial alignment with the sensing site, disposing a stimulation electrode in the blood vessel at the stimulation site, activating the stimulation electrode to evoke the CAP(s), and sequentially activating the sensing electrodes in response to the activation of the stimulation electrode, such that the eCAP(s) is sensed by the activation of one of the sensing electrodes. The method further comprises identifying the circumferential site at which the one sensing electrode is located as the sensing site. This method may further comprise disposing a plurality of therapeutic electrodes in the blood vessel respectively adjacent the sensing electrodes, and selecting the therapeutic electrode adjacent the one sensing electrode to convey the therapeutic energy to the therapeutic site. A cylindrical support structure carrying the sensing electrodes and therapeutic electrodes may be disposed in the blood vessel in axial alignment with the sensing site. In this case where hypertension is treated, and the blood vessel is a renal artery, the modulation of the nerve branch may decrease the blood pressure of the patient, thereby treating the hypertension.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
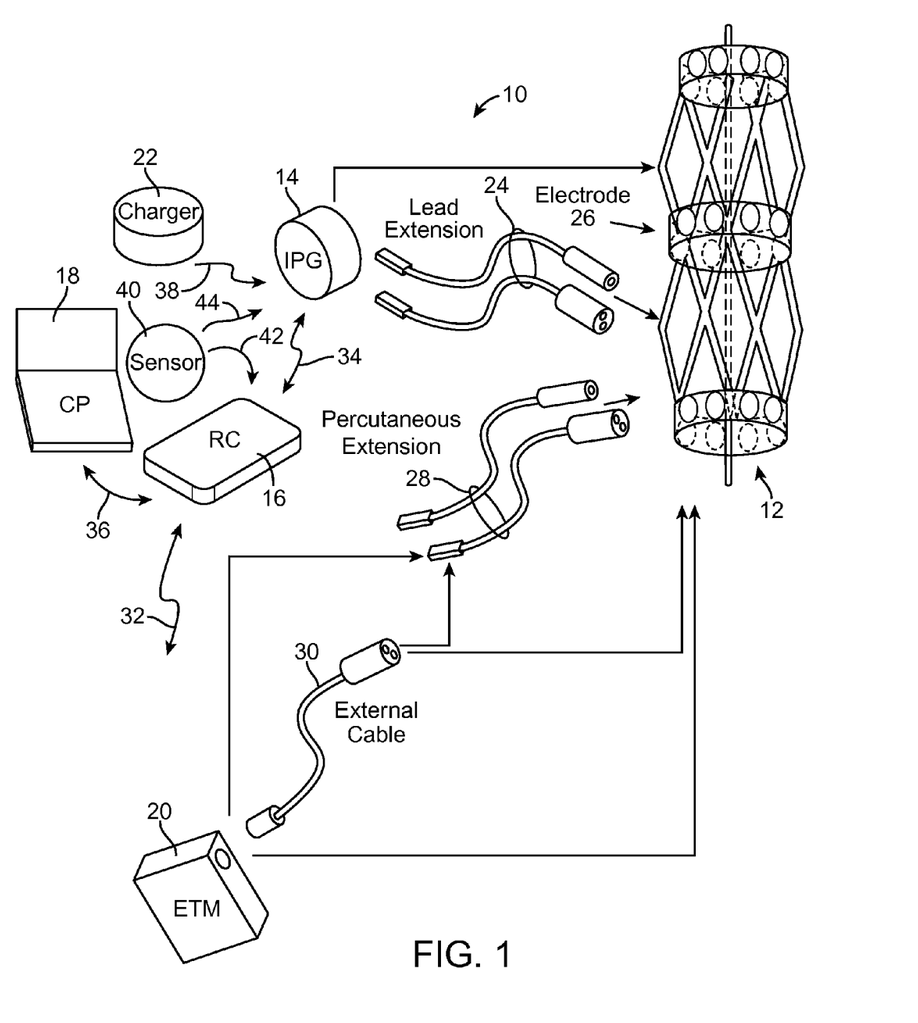
FIG. 1 is a block diagram of an exemplary neuromodulation system constructed accordance with one embodiment of the present inventions.

Turning first to FIG. 1, an exemplary neuromodulation system 10 comprises a stent lead 12, an implantable pulse generator (IPG) 14 (or alternatively RF receiver-stimulator), an external remote control (RC) 16, a Clinician's Programmer (CP) 18, an External Trial Stimulator (ETM) 20, and an external charger 22.

The IPG 14 is physically connected via a lead extension 24 to the stent lead 12, which carries a plurality of circumferentially disposed electrodes 26. The IPG 14 delivers electrical neuromodulation energy in the form of a pulsed electrical waveform (i.e., a temporal series of electrical pulses) to the electrodes 26 in accordance with a set of neuromodulation parameters.

The ETM 20 may also be physically connected via the percutaneous lead extension 28 and external cable 30 to the stent lead 12. The ETM 20, which has similar pulse generation circuitry as the IPG 14, also delivers electrical neuromodulation energy in the form of a pulse electrical waveform to the array of electrodes 26 in accordance with a set of neuromodulation parameters. The major difference between the ETM 20 and the IPG 14 is that the ETM 20 is a non-implantable device that is used on a trial basis after the stent lead 12 have been implanted and prior to implantation of the IPG 14, to test the responsiveness of the electrical energy that is to be provided. Thus, it should be understood that all functionalities of the IPG 14 described herein can also be implemented with the ETM 20 to the extent that such functionalities are not dependent on the device being implanted within the patient's body.

The RC 16 may be used to telemetrically control the ETM 20 via a communications link 32. Once the IPG 14 and stent lead 12 are implanted, the RC 16 may be used to telemetrically control the IPG 14 via a communications link 34. Such control allows the IPG 14 to be turned on or off and to be programmed with different neuromodulation parameter sets.

The IPG 14 may also be operated to modify the programmed neuromodulation parameters to actively control the characteristics of the electrical neuromodulation energy output by the IPG 14.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed neuromodulation parameters provided by the CP 18 are also used to program the RC 16, so that the neuromodulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present. For purposes of brevity, the details of the RC 16, CP 18, ETM 20, and external charger 22 will not be described herein. Details of exemplary embodiments of these devices are disclosed in U.S. Pat. No. 6,895,280, which is expressly incorporated herein by reference.

The neuromodulation system 10 further includes one or more blood pressure sensors 40. The sensor 40 may be implanted within the patient's body, or one could employ a sensor 40 capable or remotely sensing the desired factor from a position outside the patient's body.

A number of conventional pressure sensing devices and techniques are available to be used as the sensor 40. To sense blood pressure, for example, one could choose from among sensors based on mechanical, piezoelectric, micro-electro-mechanical-system (MEMS), electromagnetic, or other technologies. In some embodiments, other types of sensors that measure parameters correlatable to blood pressure (e.g., EKG using beat-to-beat (R-R) variability to globally assess autonomic tone) may also be used. By way of a non-limiting example, an intraluminal catheter filled with saline that is continuous with a sensor based in the IPG 14, such as a piezoresistive strain gage, may be used to measure the blood pressure of the patient. The saline would transfer the pressure back to the strain gage. Also, a strain gage built into the stent itself inside the renal artery may be used to directly measure intraluminal pressure. In this case, the stent lead 12 could be placed such that this strain gage is as close as possible to the origin of the renal artery at the abdominal aorta to minimize artifacts in the blood pressure measurement. Alternatively, the sensor 40 can take the form of one or more electrodes on the stent lead 12, or one or more electrodes on a separate stent lead 12. In the latter case, the electrodes can be used to measure neural firing activity (e.g., evoked compound action potentials (eCAP)) at the carotid baroreceptors or transverse aortic arch baroreceptors in order to calculate the blood pressure (e.g., analogous to the body's own blood pressure control mechanism).

In either instance, the sensor 40 (or the electrodes 26) can provide the observed data (e.g., patient's blood pressure) to the IPG 14 and/or the external RC 16. If the separate sensor 40 is used, the observed data can be provided to the IPG 14 and/or the external RC 16 via communication links 44 and/or 42, respectively, or via an electrical conductor (not shown). The communication links 44 and 42 may be implemented with any suitable communication technologies, including but not limited to radio frequency, infrared, electromagnetic, and/or induction based communication links.

The IPG 14 is configured to analyze the sensed blood pressure and make appropriate adjustment to the neuromodulation therapy by alternatively turning the neuromodulation therapy on or off. For example, the IPG 14 can be configured to compare the sensed blood pressure to both a first threshold (e.g., 140 mm Hg systolic/90 mm Hg diastolic) and a second threshold (e.g., somewhere in a range of 100-140 mm Hg systolic/60-90 mm Hg). If the comparison reveals that the detected blood pressure is above the first threshold, and the IPG 14 is currently not modulating the renal nerve branch, the IPG 14 can automatically initiate the therapeutic neuromodulation of the renal nerve branch. If the detected blood pressure is below the second threshold, and the IPG 14 is currently modulating the renal nerve branch, the IPG 14 can automatically cease the neuromodulation of the renal nerve branch.

In addition to initiating and/or ceasing the delivery of the therapeutic neuromodulation energy, the IPG 14 can be optionally configured to adjust the neuromodulation parameters based on the sensed blood pressure. For example, the IPG 14 can adjust the electrode combination (which may be fractional ized) to steer the therapeutic neuromodulation energy on different electrodes 26 that show better therapeutic results. Similarly, an electrical pulse parameter can be adjusted so that optimal therapeutic neuromodulation energy is delivered at the correct location of the renal nerve branches, thereby maintaining the patient's blood pressure at the desired level.

The IPG 14 is also configured for delivering electrical stimulation energy to selected ones of the electrodes 26, thereby evoking compound action potentials (eCAPs) within nerves, sensing the eCAPs at selected ones of the electrodes 26, and delivering therapeutic neuromodulation energy to selected ones of the electrodes 26. As will be described in detail later below, the IPG 14 identifies the electrodes that are adjacent (or sufficiently close) to the nerve branches based on the eCAP measurements. The IPG 14 then uses those identified electrodes as reference points to deliver therapeutic neuromodulation energy to adjacent nerve branches.

Instead of the IPG 14, external programming devices, such as the RC 16 and/or the CP 18, may be configured to analyze the sensed blood pressure, initiate or cease the neuromodulation therapy, optionally adjusting the neuromodulation parameters, and/or identifying nerve branches.

Figure 2:
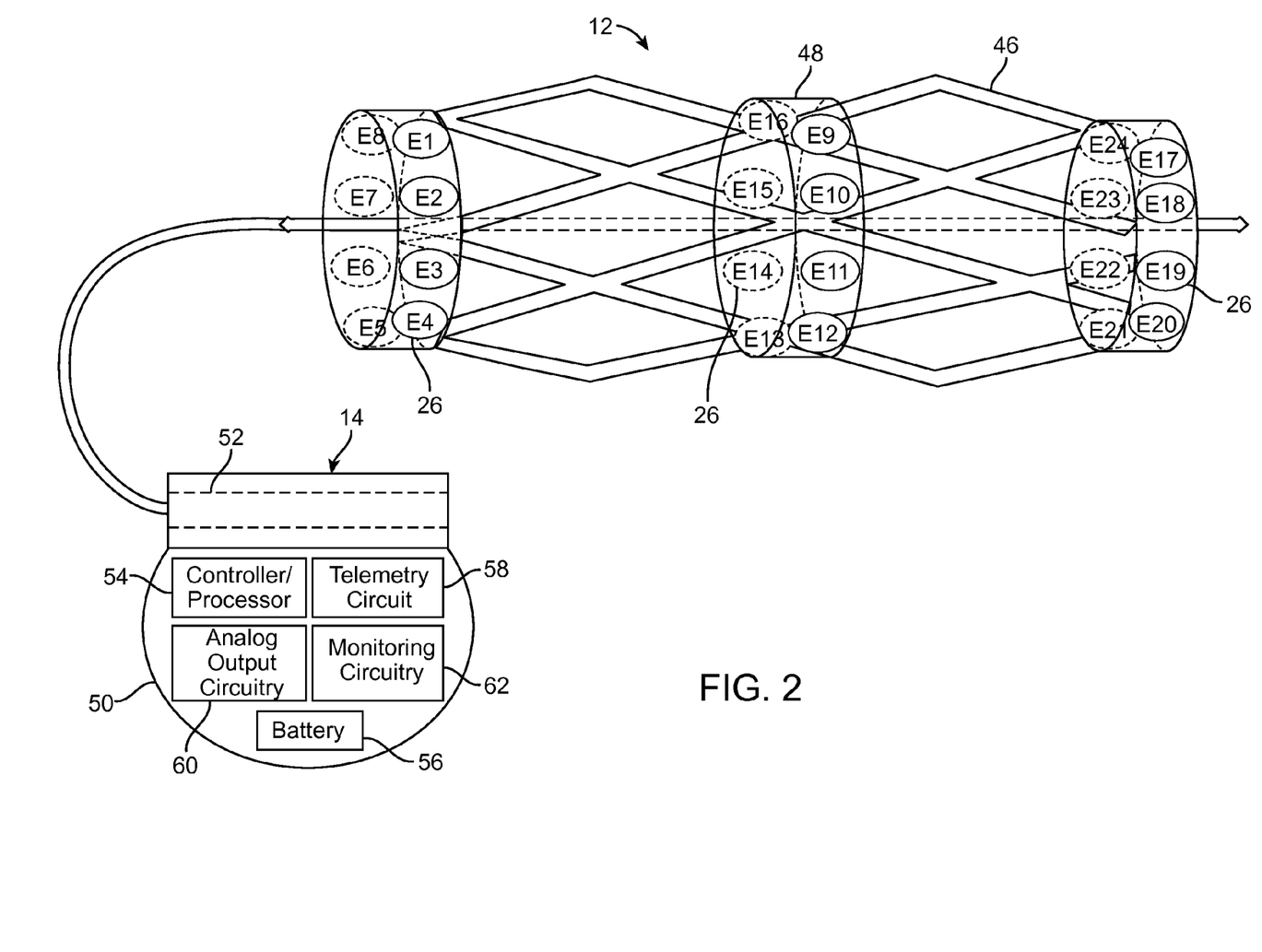
FIG. 2 is a plan view of an implantable pulse generator (IPG) and an exemplary stent lead used in the neuromodulation system of FIG. 1.

Referring now to FIG. 2, an exemplary stent lead 12 and IPG 14 will be described. The stent lead 12 comprises a lead wire 45 and a cylindrical support structure 46 configured for being deployed in a blood vessel of the patient. The electrodes 26, which may function as stimulation electrodes, sensing electrodes and/or therapeutic electrodes, are circumferentially and axially disposed about the cylindrical support structure 46. By way of non-limiting example, the cylindrical support structure 46 carries twenty-four electrodes 26, arranged as three rings of electrodes axially located relative to each other (the first ring A consisting of electrodes E1-E8; the second ring B consisting of electrodes E8-E16; and the third ring C consisting of electrodes E17-E24). The actual number of electrodes will, of course, vary according to the intended application.

In one embodiment, each of the electrodes 26 may be configured as either a stimulation electrode, sensing electrode or a therapeutic electrode. In another embodiment, all of the electrodes located on a ring, such as the ring A, are dedicated stimulation (or neuromodulation) electrodes, and all of the electrodes located on a separate ring, such as the ring C, are dedicated sensing electrodes. Alternatively, the odd-numbered electrodes on each ring may be dedicated stimulation (or neuromodulation) electrodes, and the even-numbered electrodes on each ring may be dedicated sensing electrodes.

The cylindrical support structure 46 takes the form of a resilient skeletal spring structure that allows it to be collapsed into low-profile geometry to facilitate convenient delivery of the stent lead 12 into the blood vessel, and spring open or expand for urging the electrodes 26 against an inner wall of the blood vessel. The resilient skeletal spring structure 46 may be made from a wire having a relatively high-stiffness and resilient material or a high-stiffness urethane or silicone, that is shaped into a three-dimensional geometry. In an alternative embodiment, the cylindrical support structure 46 takes the form of a balloon that can expand from a low-profile geometry to an expanded geometry.

The electrodes 26 are disposed on the outer surface of the cylindrical support structure 46. In this setting, when the cylindrical support structure 46 is expanded within the blood vessel, all the electrodes 26 are arranged to point outward from the cylindrical support structure 46 and deliver stimulation energy to the vessel wall (in order to evoke compound action potentials (CAPs) in nerve branches associated with the vessel as will be described in further detail below), sense physiological information from the vessel wall (in order to sense the evoked CAPs (eCAPs) from the nerve branches associated with the vessel as will be described in further detail below), and/or deliver therapeutic neuromodulation energy to the vessel wall (in order to modulate the nerve branches associated with the vessel as will be described in further detail below). The regions where the electrodes 26 configured as the stimulation electrodes, sensing electrodes, and therapeutic electrodes come in contact with the inner wall of the blood vessel are called as stimulation sites, sensing sites, and therapeutic sites, respectively.

The stent lead 12 further comprises an electrical insulation structure 48 disposed on the luminal surface of the cylindrical support structure 46 for preventing the electrical energy from being radially conveyed inward from the electrodes 26 to the blood and for preventing physiological information from being sensed from the blood. The electrical insulation structure 48 may be made of a flexible electrical insulation layer formed of a relatively thin (e.g., 0.1 mm to 2 mm, although 1 mm or less is most preferred) and relatively low-stiffness material. Exemplary materials are low-stiffness silicone, expanded polytetrafluoroethylene (ePTFE), or urethane. Further details describing the construction and method of manufacturing stent lead are disclosed in U.S. Patent Publication. No. 2012/0059446 A1, entitled "Collapsible/Expandable Tubular Electrode Leads," which is expressly incorporated herein by reference.

The IPG 14 includes an outer case 50 for housing the electronic and other components (described in further detail below). The outer case 50 is composed of an electrically conductive, biocompatible material, such as titanium, and forms a hermetically sealed compartment, wherein the internal electronics are protected from the body tissue and fluids. In some cases, the outer case 50 may serve as an electrode. The IPG 14 further comprises a connector 52 to which the proximal ends of the stent lead 12 mates in a manner that electrically couples the electrodes 26 to the internal electronics (described in further detail below) within the outer case 50. To this end, the connector 52 includes a port (not shown) for receiving the proximal end of the stent lead 12. In the case where the lead extension 24 (shown in FIG. 1) is used, the port may instead receive the proximal end of such lead extension 24.

The IPG 14 comprises electronic components, such as a controller/processor 54, a battery 56, a telemetry circuitry 58, analog output circuitry 60, monitoring circuitry 62, and other suitable components known to those skilled in the art.

Telemetry circuitry 58, including an antenna (not shown), is configured for receiving programming data (e.g., the operating program and/or neuromodulation parameters) from the RC 16 in an appropriate modulated carrier signal, and demodulating the carrier signal to recover the programming data, which the programming data is then stored in the memory (not shown). The battery 56, which may be a rechargeable lithium-ion or lithium-ion polymer battery, provides operating power to IPG 14.

The analog output circuitry 60 provides electrical energy in the form of a pulsed electrical waveform to the electrodes 26 in accordance with a set of neuromodulation parameters programmed into the IPG 14 either for the purposes of evoking CAPs to identify the nerve branches or modulating the nerve branches (either stimulating the nerve branches or blocking/disrupting activity in the nerve branches). Such neuromodulation parameters may comprise electrode combinations, which define the electrodes that are activated as anodes (positive), cathodes (negative), and turned off (zero), percentage of electrical energy assigned to each electrode of the array of electrodes 26 (fractionalized electrode configurations), and electrical pulse parameters, which define the pulse amplitude (measured in milliamps or volts depending on whether the IPG 14 supplies constant current or constant voltage to the array of electrodes 26), pulse width (measured in microseconds), pulse rate (measured in pulses per second), and burst rate (measured as the neuromodulation on duration X and neuromodulation off duration Y).

Electrical neuromodulation will occur between two (or more) activated electrodes, one of which may be the IPG case 44. Simulation energy may be transmitted to the tissue in a monopolar or multipolar (e.g., bipolar, tripolar, etc.) fashion. Monopolar neuromodulation occurs when a selected one of the lead electrodes 26 is activated along with the case 44 of the IPG 14, so that electrical energy is transmitted between the selected electrode 26 and the case 44. Bipolar neuromodulation occurs when two of the lead electrodes 26 are activated as anode and cathode, so that electrical energy is transmitted between the selected electrodes 26. For example, an electrode on one lead 12 may be activated as an anode at the same time that an electrode on the same lead or another lead 12 is activated as a cathode. Tripolar neuromodulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The electrical energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) neuromodulation pulse and an anodic (positive) recharge pulse that is generated after the neuromodulation pulse to prevent direct current charge transfer through the tissue, thereby avoiding electrode degradation and cell trauma. That is, charge is conveyed through the electrode-tissue interface via current at an electrode during a neuromodulation period (the length of the neuromodulation pulse), and then pulled back off the electrode-tissue interface via an oppositely polarized current at the same electrode during a recharge period (the length of the recharge pulse).

The monitoring circuitry 62 is configured for monitoring status of various nodes and parameters throughout the IPG 14, e.g., power supply voltages, temperature, and the like. More significantly, the monitoring circuitry 62 is configured for sensing eCAPs at the sensing electrodes 26 and acquiring blood pressure data from the sensor 40.

The controller/processor 54 executes a suitable program stored in memory (not shown) for controlling the stimulation output circuitry 60 and monitoring circuitry 62 to evoke and sense eCAPs in nerve branches associated with a blood vessel, identifying target sites on the nerve branches based on the sensed eCAPs, and controlling the stimulation output circuitry 60 to modulate the identified target sites in response to the sensed blood pressure data. In performing these functions, the controller/processor 54 configures (to the extent that the electrodes 26 are reconfigurable) selected ones of the electrodes 26 as stimulation electrodes, sensing electrodes, and therapeutic electrodes at the appropriate times. The controller/processor 54 also executes the program for controlling the stimulation output circuitry 60 and the sensor 40 to modulate the nerve branches based on the monitored blood pressure.

The controller/processor 54 is configured for performing at least one of two techniques for identifying a renal nerve branch to be modulated.

In the first technique, the controller/processor 54 prompts the stimulation output circuitry 60 to sequentially activate the stimulation electrodes located on one of the rings (A, B, or C) to evoke at least one CAP in one of the renal nerve branches. The controller/processor 54 prompts the monitoring circuitry 62 to simultaneously activate the sensing electrodes located on a different one of the rings (A, B, or C) (or alternatively, a single ring electrode (not shown)) in response to the sequential activation of each of the stimulation electrodes.

At least one of the sensing electrode(s) senses the eCAP(s), and based on this sensing, the controller/processor 54 identifies at least one of the stimulation electrodes located adjacent to the nerve branch. That is, the stimulation electrode that evoked the CAP that was sensed by one of the sensing electrodes will be identified as the electrode that is adjacent the nerve branch. To increase the signal-to-noise ratio, the multiple CAPs may be evoked by each stimulation electrode and sensed by the sensing electrode(s). The controller/processor 54 may then average the magnitudes of multiple CAPs evoked by each stimulation electrode, and then use this average to identify the stimulation electrode(s) that are located adjacent to the nerve branch.

The controller/processor 54 prompts the stimulation output circuitry 60 to deliver therapeutic neuromodulation energy to the therapeutic electrode adjacent the identified stimulation electrode, thereby modulating the nerve branch. The therapeutic electrode may be the identified stimulation electrode, one of the electrodes adjacent the identified stimulation electrode, or even two electrodes circumferentially flanking the identified stimulation electrode. In the latter case, the two electrodes may be operated in a bipolar manner to modulate the tissue, including the nerve branch, located between the two therapeutic electrodes.

In the second technique, the controller/processor 54 prompts the stimulation output circuitry 60 to simultaneously activate the stimulation electrodes located on one of the rings (A, B, or C) (or alternatively, a single ring electrode (not shown) to evoke at least one CAP in one of the renal nerve branches. The controller/processor 54 prompts the monitoring circuitry 34 to sequentially activate the sensing electrodes located on a different one of the rings (A, B, or C) in response to the simultaneous activation of the stimulation electrodes.

At least one of the sensing electrode(s) senses the eCAP(s), and based on this sensing, the controller/processor 54 identifies at least one of the sensing electrodes located adjacent to the nerve branch. That is, the sensing electrode that sensed the eCAP that was evoked by one of the stimulation electrodes will be identified as the electrode that is adjacent the nerve branch. To increase the signal-to-noise ratio, the multiple eCAPs may be sensed by each of the sensing electrodes. The controller/processor 54 may then average the magnitudes of the multiple CAPs sensed by each sensing electrode, and then use this average to identify the sensing electrode(s) that are located adjacent to the nerve branch.

The controller/processor 54 prompts the stimulation output circuitry 60 to deliver therapeutic neuromodulation energy to the therapeutic electrode adjacent the identified sensing electrode, thereby modulating the nerve branch. The therapeutic electrode may be the identified sensing electrode, one of the electrodes adjacent the identified sensing electrode, or even two electrodes circumferentially flanking the identified sensing electrode. In the latter case, the two electrodes may be operated in a bipolar manner to modulate the tissue, including the nerve branch, located between the two therapeutic electrodes.

Figure 3:
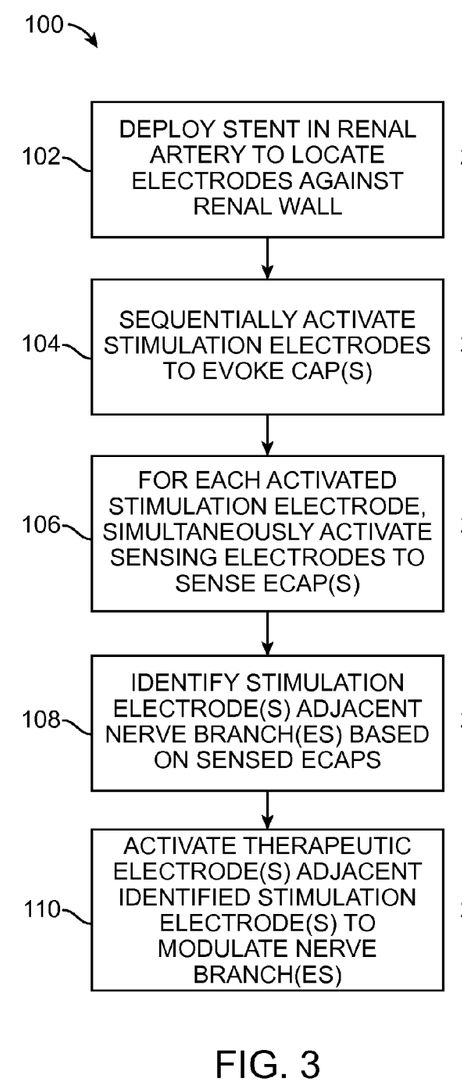
FIG. 3 is a flow diagram illustrating one method of using the neuromodulation system of FIG. 1 to identify and modulate renal nerve branches, thereby treating the hypertension of a patient.

Having described the structure and function of the neuromodulation system 10, one method 100 of using the system 10 to treat hypertension in a patient will now be described with reference to FIG. 3. Although this method is described in the context of treating hypertension, it should be appreciated that the method can be modified to treat various other medical conditions, such as those pertaining pulmonary and cardiac diseases.

Figure 5:
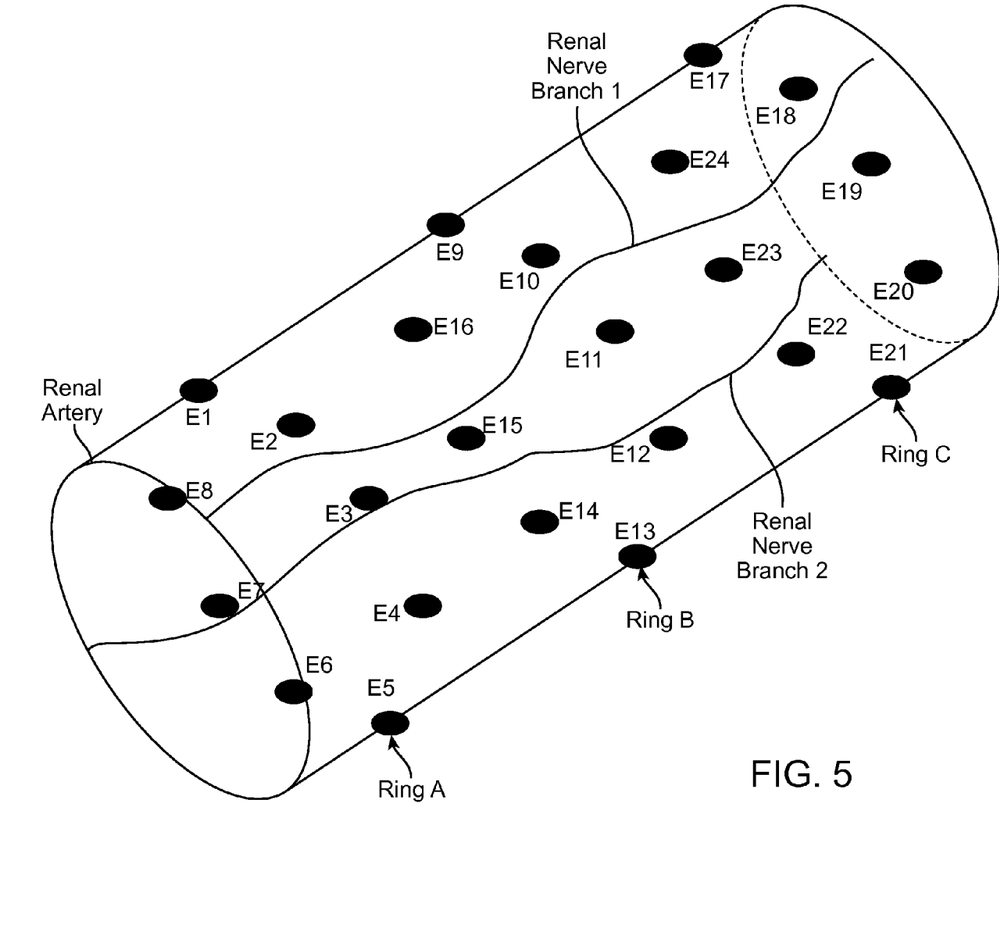
FIG. 5 is a perspective view illustrating the stent lead of the neuromodulation system of FIG. 1 deployed within a renal artery of the patient.

At step 102, the support structure 24 of the stent catheter 12 is deployed in the renal artery in a conventional manner. In particular, the support structure 24, while in the collapsed state, is advanced through a guide sheath (not shown) and placed into the renal artery. As the support structure 24 is advanced from the distal end of the guide sheath, it expands to firmly place the electrodes 26 against the inner wall of the blood vessel. Thus, the three electrode rings (A, B, and C) are disposed in the renal artery, as illustrated in FIG. 5. In this example, the electrode ring A will be used to evoke the CAPs, whereas the electrode ring C will be used to sense the eCAPs. In this case, electrodes E1-E8 will be disposed at a plurality of circumferential stimulation sites within the renal artery, and electrodes E17-E24 will be disposed at a plurality of sensing sites within the renal artery axially remote from the circumferentially disposed stimulation sites. Alternatively, if a single sensing ring electrode is used, it will be disposed at a single circumferential sensing site axially remote from the circumferentially disposed stimulation sites. In this technique, the therapeutic electrodes will be disposed in axial alignment with the circumferentially disposed stimulation sites within the renal artery. In the illustrated method, the therapeutic electrodes are identical to the ring of stimulation electrodes E1-E8, and thus, the stimulation sites are equivalent to the therapeutic sites. However, as previously discussed above, the ring of electrodes may alternate between stimulation electrodes and therapeutic electrodes (e.g., stimulation electrodes being electrodes E1, E3, E5, and E7; and therapeutic electrodes being electrodes E2, E4, E6, and E8), in which case, the therapeutic sites and the stimulation sites will alternate between each other.

It is contemplated that at least one of the stimulation electrodes and at least one of the sensing electrodes will be located adjacent to a nerve branch within the wall of the blood vessel. In the example illustrated in FIG. 5, one nerve branch (nerve branch 1) extends along the renal artery in proximity to stimulation electrode E2 and sensing electrode E18, and another nerve branch (nerve branch 2) extends along the renal artery in proximity to stimulation electrode E7 and sensing electrode E23. It should be noted the stimulation electrode and sensing electrode that are adjacent a particular renal nerve branch may not be on the same circumferential location. For example, stimulation electrode E7 and sensing electrode E23 are circumferentially offset from each other by one electrode.

Next, at step 104, the controller/processor 54 prompts the analog output circuitry 60 to sequentially activate the stimulation electrodes one-at-a-time to deliver the electrical stimulation energy to the wall of the renal artery at the respective stimulation sites. If any nerve branch is present at any of the stimulation sites, the stimulation energy depolarizes that nerve branch, thereby evoking a CAP that propagates along the nerve branch. For example, delivering the electrical stimulation energy from electrodes E2 and E7 should respectively evoke CAPs in nerve branches 1 and 2. Such stimulation is supra-threshold, but should not be uncomfortable for a patient. A suitable stimulation pulse is, for example, 4 mA for 200 μs.

The controller/processor 54 optionally prompts the analog output circuitry 60 to activate each stimulation electrode multiple times to deliver the electrical stimulation energy to the wall of the renal artery at each stimulation site. In this case, each stimulation electrode may be activated multiple times without any intervening activation of other stimulation electrodes, or the stimulation electrodes may be cyclically activated multiple times. In either event, each stimulation electrode may be activated multiple times. If the nerve branch is present at any stimulation site, multiple CAPs will be evoked at this stimulation site.

At step 106, in response to the activation of each stimulation electrode, the controller/processor 54 prompts the monitoring circuitry 34 to simultaneously activate the sensing electrodes (or alternatively, activated a ring electrode) to sense the eCAP(s) at the sensing site(s). In the case where the stimulation electrodes are activated multiple times to evoke multiple eCAP(s) in the nerve branches for each sensing electrode, the multiple eCAPs that are sensed will be averaged to increase the signal-to-noise ratio of all eCAPs sensed by the sensing electrodes.

In the illustrated example, stimulation electrode E1 will be activated, but will not evoke an eCAP, since it is not adjacent any of nerve branches 1 and 2. In response, the sensing electrodes E17-E24 will be activated, but will not sense an eCAP since none has been evoked. Stimulation electrode E2 will then be activated, and will evoke an eCAP, since it is adjacent nerve branch 1. In response, the sensing electrodes E17-E24 will be activated, and will sense the eCAP. This process is repeated for each of remaining electrodes E3-E8, with electrodes E3-E6 and E8 not evoking an eCAP, since none are adjacent the any of nerve branches 1 and 2, and electrode E7 will evoke an eCAP, since it is adjacent nerve branch 2. It can be determined from this that electrodes E2 and E7 are respectively adjacent nerve branches 1 and 2.

At step 108, the controller/processor 54 identifies the stimulation electrode that evoked the CAP, and thus, the circumferential location of the nerve branch. That is, the stimulation electrode that evoked the CAP that was sensed by any of the sensing electrodes will be deemed the stimulation electrode that is adjacent the nerve branch. In the illustrated embodiment, electrodes E2 and E7 will be identified as the stimulation electrodes that are adjacent respective nerve branches 1 and 2.

At step 110, the controller/processor 54 prompts the analog output circuitry 60 to deliver therapeutic neuromodulation energy to the therapeutic electrode(s) adjacent the identified stimulation site(s) (i.e., the stimulation site(s) that are adjacent the renal nerve branch(es)). As previously discussed above, the therapeutic electrode may be any of the electrodes E1-E8, and in this case, electrodes E2 and E7, which may be activated in a monopolar manner in conjunction with the patch electrodes to modulate nerve branches 1 and 2. In the case where only odd electrodes are used as stimulation electrodes, and even electrodes are used as therapeutic electrodes, the stimulation electrodes that may be identified as being adjacent to the nerve branches may be electrodes E3 and E7. In this case, electrodes E2 and E4 may be activated in a bipolar manner to modulate nerve branch 1, and electrodes E6 and E8 can be activated in a bipolar manner to modulate nerve branch 2.

Figure 4:
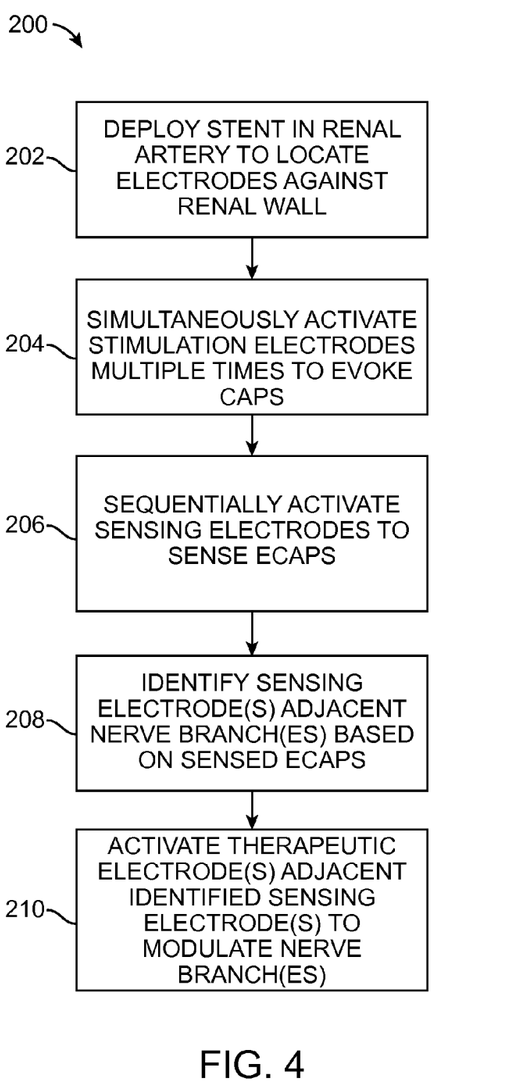
FIG. 4 is a flow diagram illustrating another method of using the neuromodulation system of FIG. 1 to identify and modulate renal nerve branches, thereby treating the hypertension of a patient.

Another method 200 of using the system 10 to treat hypertension in a patient will now be described with reference to FIG. 4. The method 200 is similar to the method 100 with the exception that the therapeutic neuromodulation energy is delivered to sensing sites that are adjacent to the renal nerve branches.

At step 202, support structure 24 of the stent catheter 12 is deployed in the renal artery in the same manner described above with respect to step 102. Next, at step 204, the controller/processor 54 prompts the analog output circuitry 60 to simultaneously activate the stimulation electrodes (or alternatively, a single ring electrode) multiple times to deliver the electrical stimulation energy to the wall of the renal artery at the respective stimulation sites. The stimulation energy depolarizes the nerve branches, thereby evoking CAPs that propagate along each nerve branch. At step 206, in response to the activation of the stimulation electrodes, the controller/processor 54 prompts the monitoring circuitry 34 to sequentially activate the sensing electrodes (to sense the eCAPs at the sensing sites. That is, each time the stimulation electrodes are simultaneously activated, a different one of the sensing electrodes is activated.

For each sensing electrode, the controller/processor 54 optionally prompts the analog output circuitry 60 to activate the stimulation electrodes multiple times to deliver the electrical stimulation energy to the wall of the renal artery at the stimulation sites, thereby evoking multiple CAPs at each of the renal nerve branches. The multiple eCAPs that are sensed will be averaged to increase the signal-to-noise ratio of all eCAPs sensed by each sensing electrode.

In the illustrated example, stimulation electrodes E1-E8 will be activated to evoke eCAPs in nerve branches 1 and 2. In response, sensing electrode E17 may be activated, but will not sense the evoked eCAPs, since it is not adjacent nerve branches 1 and 2. Stimulation electrodes E1-E8 will be activated again to evoke eCAPs in nerve branches 1 and 2. In response, sensing electrode E18 may be activated, and will sense an evoked eCAP, since it is adjacent nerve branch 1. This process is repeated for each of remaining sensing electrodes E19-E24, with sensing electrodes E19-E21, and E23-E24 not sensing an eCAP, since that are not adjacent nerve branches, and sensing electrode E22 sensing an eCAP, since it is adjacent nerve branch 2. It can be determined from this that electrodes E18 and E22 are respectively adjacent nerve branches 1 and 2.

At step 208, the controller/processor 54 identifies the sensing electrode that sensed the CAP, and thus, the circumferential location of the nerve branch. That is, the sensing electrode that sensed the CAP that was evoked by any of the stimulation electrodes will be deemed the sensing electrode that is adjacent the nerve branch. In the illustrated embodiment, electrodes E18 and E22 will be identified as the sensing electrodes that are adjacent respective nerve branches 1 and 2.

At step 210, the controller/processor 54 prompts the analog output circuitry 60 to deliver therapeutic electrical energy to the therapeutic electrode(s) adjacent the identified sensing site(s) (i.e., the sensing site(s) that are adjacent the renal nerve branch(es)). As previously discussed above, the therapeutic electrode may be any of the electrodes E17-E24, and in this case, electrodes E18 and E22, which may be activated in a monopolar manner in conjunction with the patch electrodes to modulate nerve branches 1 and 2. In the case where only odd electrodes are used as stimulation electrodes, and even electrodes are used as therapeutic electrodes, the sensing electrodes that may be identified as being adjacent to the nerve branches may be electrodes E19 and E23. In this case, electrodes E18 and E20 may be activated in a bipolar manner to modulate nerve branch 1, and electrodes E22 and E24 can be activated in a bipolar manner to modulate nerve branch 2. As a result of the modulation of the renal nerve branch(es), the blood pressure of the patient will be lowered, thereby treating the hypertension. The therapeutic electrical energy may be delivered in accordance with any one of the two approaches described above.

Figure 6:
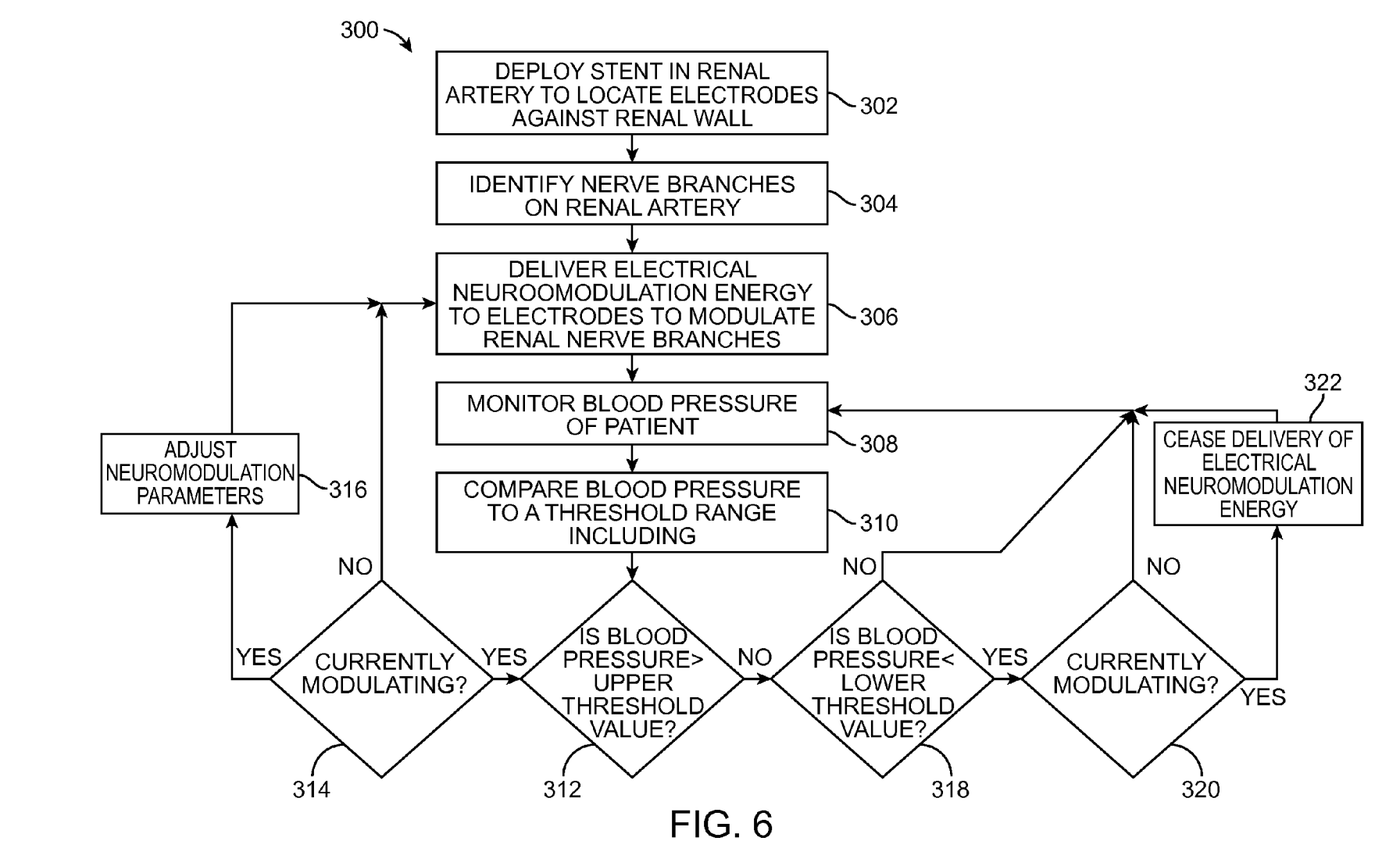
FIG. 6 is a flow diagram illustrating a method of using the neuromodulation system of FIG. 1 to modulate renal nerve branches based on a sensed blood pressure, thereby chronically treating the hypertension of a patient.

One method 300 of using the neuromodulation system 10 to chronically treat hypertension will now be described with respect to FIG. 6.

The support structure 24 of the stent catheter 12 is deployed in the renal artery (step 302), and renal nerve branches are identified in the same manner described above with respect to methods 100 and 200 (step 304). Once the locations of the renal nerve branches are identified, the controller/processor 54 prompts the analog output circuitry 60 to deliver the therapeutic electrical neuromodulation energy to the electrodes 26 adjacent to the identified locations and modulate the renal nerve branches according to a set of neuromodulation parameters to treat the patient's hypertension (step 306).

In particular, the neuromodulation system 10 may be configured modulating the renal nerve in an attempt to disrupt the sympathetic nerves, thereby affecting the patient's blood pressure. Neuromodulation of the renal nerve may reduce sympathetic tone, which in turn has an electrical sympatholytic effect, reducing the patient's blood pressure. That is, neuromodulation of the sympathetic renal nerve branches may block action potentials that down-regulate the sympathetic nervous system, resulting in vasodilation, thus decreasing the patient's blood pressure. Alternatively, neuromodulation of the parasympathetic renal nerve branches may evoke action potentials that up-regulate the parasympathetic nervous system, resulting in vasodilation, thus decreasing the patient's blood pressure. Thus, it can appreciated that neuromodulation of the renal nerve branches (which includes both sympathetic and parasympathetic nerves) may decrease the patient's blood pressure.

Thus, there are two variables affecting the renal nerve branch neuromodulation step are the type of nerve branches (either sympathetic or parasympathetic) and the particular neuromodulation parameters used to either evoke action potentials or block action potentials along the renal nerve branches. For example, neuromodulation of a renal nerve at a pulse rate less 500 Hz may evoke action potentials in the renal nerve, whereas neuromodulation of the renal nerve at a pulse rate greater than 1 KHz may block action potentials in that nerve fiber. By modulating the renal nerve branches as opposed to ablating them, permanent damage to the renal artery wall can be prevented.

Although the modulating the nerve branches can be an effective way of treating the hypertension in an open-loop fashion, the optimal control of blood pressure by such therapeutic intervention may benefit from a closed loop control. Accordingly, the neuromodulation system 10 operates in a closed-loop manner to automatically adjust the neuromodulation to the renal nerve branch based on blood pressure sensed by a sensor 40. In this regard, the neuromodulation system 10 continually (either continuously or periodically) monitors the blood pressure of the patient (step 308). As briefly mentioned above, the pressure may be measured by sensing the magnitude of eCAPs naturally evoked by carotid baroreceptors and/or transverse aortic arch baroreceptors caused by intraluminal pressure changes in the carotid artery or transverse aortic arch, or can be measured anywhere in the body, including the renal artery, by piezoresistive strain gage, such as a MEMS.

In response to each blood pressure measurement via the sensor 40, the controller/processor 54 compares the obtained blood pressure to a threshold range that includes both an upper threshold value (e.g., 140 mm Hg systolic/90 mm Hg diastolic) and a second threshold value (e.g., somewhere in a range of 100-140 mm Hg systolic/60-90 mm Hg) (step 310). If the comparison reveals that the detected blood pressure is above the upper threshold value (step 312), the controller/processor 54 determines whether or not the analog output circuitry 60 is currently modulating the renal nerve branches (step 314). If the analog output circuitry 60 is currently not modulating the renal nerve branches, the controller/processor 54 automatically prompts the analog output circuitry 60 to initiate neuromodulation of the renal nerve (step 306). However, if the analog output circuitry 60 is currently modulating the renal nerve branches, the controller/processor 54 adjusts one or more neuromodulation parameters in an effort to decrease the patient's blood pressure (step 316), and prompts the analog output circuitry 60 to modulate the renal nerve branches in accordance with the new neuromodulation parameters (step 306). For example, the controller/processor 54 may adjust one or more neuromodulation parameters (e.g., a fractionalized electrode configuration, pulse amplitude, pulse duration, or pulse rate), so that optimal therapeutic neuromodulation energy is delivered at the correct intensity level and at the correct location of the renal nerve branches, thereby decreasing the patient's blood pressure at the desired level.

In contrast, if the comparison at step 310 reveals that the detected blood pressure is below the lower threshold (step 318), the controller/processor 54 determines whether or not the analog output circuitry 60 is currently modulating the renal nerve branches (step 320). If the analog output circuitry 60 is currently modulating the renal nerve branches, the controller/processor 54 automatically prompts the analog output circuitry 60 to cease modulation of the renal nerve branches (step 322). If the analog output circuitry 60 is currently not modulating the renal nerve branches, then the controller/processor 54 simply prompts the monitoring circuitry 62 to monitor the patient's blood pressure (step 308). Similarly, if the comparison at step 310 reveals that the detected blood pressure is neither above the upper threshold value nor below the lower threshold value, the controller/processor 54 simply prompts the monitoring circuitry 62 to monitor the patient's blood pressure (step 308).

Preferably, hysteresis is built into the closed feedback loop, so that the controller/processor 54 does not rapidly initiate and cease neuromodulation as the detected blood pressure varies around the first threshold. For example, the lower threshold may be substantially less than the first threshold (e.g., by 5 or 10 mmHg).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neuromodulation system for use with a patient, comprising:
    a cylindrical support structure configured for being deployed in a blood vessel of the patient;
    at least one electrode carried by the cylindrical support structure;
    an electrical insulation material disposed on a luminal surface of the cylindrical support structure, the electrical insulation structure being configured to prevent electrical energy from being radially conveyed inward from the at least one electrode;
    a sensor configured for sensing a parameter correlatable to blood pressure of a patient; and
    analog output circuitry configured for conveying electrical therapeutic energy to the at least one electrode; and
    a controller/processor coupled to the sensor and the analog output circuitry, the controller/processor configured to compare the sensed parameter to a first threshold, and based on the comparison, prompt the analog output circuitry to adjust the electrical therapeutic energy being conveyed to the at least one electrode if therapeutic energy is being conveyed at the time that the controller/processor performs the comparison, and
        prompt the analog output circuitry to convey the electrical therapeutic energy to the at least one electrode if therapeutic energy is not being conveyed at the time that the controller/processor performs the comparison.

2. The neuromodulation system of claim 1, wherein the cylindrical support structure is a resilient skeletal spring structure for urging the at least one electrode against an inner wall of the blood vessel.

3. The neuromodulation system of claim 1, wherein the electrically insulative material is further configured to prevent physiological information being sensed from the blood, and the electrically insulative material comprises at least one of silicone, expanded polytetrafluoroethylene, and urethane.

4. The neuromodulation system of claim 1, wherein the cylindrical support structure comprises one of a stent and a balloon.

5. The neuromodulation system of claim 1, wherein the sensor is carried by the cylindrical support structure.

6. The neuromodulation system of claim 1, wherein the sensor includes a micro-electro-mechanical-system (MEMS) capable of measuring the parameter.

7. The neuromodulation system of claim 6, wherein the MEMS is a piezoresistive strain gage.

8. The neuromodulation system of claim 7, further comprising an intraluminal catheter configured for being filled with a liquid in communication with the piezoresistive strain gage.

9. The neuromodulation system of claim 1, wherein the sensed parameter comprises the blood pressure, the first threshold comprises a first threshold blood pressure, and the controller/processor is configured for prompting the analog output circuitry to convey the electrical therapeutic energy to the at least one electrode when the sensed blood pressure is greater than the first threshold blood pressure.

10. The neuromodulation system of claim 9, wherein the first threshold blood pressure is 140 mm Hg systolic/90 mm Hg diastolic.

11. The neuromodulation system of claim 9, wherein the controller/processor is configured for comparing the blood pressure sensed by the sensor to a second threshold blood pressure, and prompting the analog output circuitry to cease conveying the electrical therapeutic energy to the at least one electrode when the sensed blood pressure is less than the second threshold blood pressure.

12. The neuromodulation system of claim 11, wherein the second threshold blood pressure is less than the first threshold blood pressure.

13. The neuromodulation system of claim 12, wherein the second threshold blood pressure is in the range of 100-140 mm Hg systolic/60-90 mm Hg.

14. The neuromodulation system of claim 1, further comprising a biocompatible casing housing the analog output circuitry and the controller/processor.

* * * * *